United States Patent
Fong et al.

(10) Patent No.: US 7,462,752 B2
(45) Date of Patent: Dec. 9, 2008

(54) PROCESS TO CONVERT LINEAR ALKANES INTO ALPHA OLEFINS

(75) Inventors: Howard Lam-Ho Fong, Sugar Land, TX (US); Lizbeth Olivia Cisneros Trevino, Tamaulipas (MX); Brendan Dermot Murray, Houston, TX (US); Manuel Luis Cano, Houston, TX (US)

(73) Assignee: Shell Oil Company, Houston, TX (US)

( * ) Notice: Subject to any disclaimer, the term of this patent is extended or adjusted under 35 U.S.C. 154(b) by 791 days.

(21) Appl. No.: 11/109,551

(22) Filed: Apr. 19, 2005

(65) Prior Publication Data

US 2005/0245777 A1    Nov. 3, 2005

Related U.S. Application Data

(60) Provisional application No. 60/563,966, filed on Apr. 21, 2004.

(51) Int. Cl.
 *C07C 1/26* (2006.01)
(52) U.S. Cl. .................... 585/324; 585/641
(58) Field of Classification Search ............ 585/324, 585/641
See application file for complete search history.

(56) References Cited

U.S. PATENT DOCUMENTS

| | | | |
|---|---|---|---|
| 3,172,915 A | 3/1965 | Borkowskie et al. | 260/614 |
| 3,341,615 A | 9/1967 | Wulf et al. | 260/677 |
| 3,401,206 A | 9/1968 | Wulf et al. | 260/666 |
| 3,705,926 A | 12/1972 | Rumpf et al. | 260/683 R |
| 3,892,818 A | 7/1975 | Scharfe et al. | 260/676 R |
| 4,052,342 A | 10/1977 | Fernley et al. | 252/541 |
| 5,034,158 A | 7/1991 | Merrill et al. | 252/545 |
| 5,057,472 A | 10/1991 | Hertzengerg et al. | 502/66 |

(Continued)

FOREIGN PATENT DOCUMENTS

DE      767 822      10/1953

OTHER PUBLICATIONS

U.S. Appl. No. 11/109,552, filed Apr. 19, 2005, Fong et al.

(Continued)

*Primary Examiner*—Thuan Dinh Dang
(74) *Attorney, Agent, or Firm*—Donald F. Haas (57) ABSTRACT

This invention provides for a process to convert branched or linear alkanes to branched or linear alpha olefins (AO) of the same carbon number. The process comprises the steps of: a) halogenating linear alkanes, branched alkanes, or a mixture of linear and branched alkane to produce a mixture containing primary mono-haloalkanes and hydrogen halide; b) separating the hydrogen halide from the mixture and optionally neutralizing it with a metal oxide to produce a partially halogenated metal oxide and/or metal halide which may be regenerated; c) separating the primary mono-haloalkanes from the mixture; d) reacting the separated primary mono-haloalkanes with a metal oxide to produce a mixture of products that contains alpha olefins, unconverted primary mono-haloalkanes, possibly other reaction products, and a partially halogenated metal oxide and/or metal halide which may be regenerated; e) regenerating the partially halogenated metal oxide and/or metal halide to halogen and/or acid and a metal oxide (such as $Cl_2$) for recycle by reaction with air or oxygen ; and f) removing the unreacted primary mono-haloalkane from the reaction mixture and then purifying the alpha olefin.

15 Claims, 1 Drawing Sheet

U.S. PATENT DOCUMENTS

| | | | |
|---|---|---|---|
| 5,243,098 A | 9/1993 | Miller et al. | 568/893 |
| 5,389,277 A | 2/1995 | Prieto | 252/99 |
| 5,432,152 A | 7/1995 | Dawson et al. | 507/103 |
| 5,589,442 A | 12/1996 | Gee et al. | 507/103 |
| 5,821,394 A | 10/1998 | Schoebrechts et al. | 570/227 |
| 5,849,960 A | 12/1998 | Singleton et al. | 568/909 |
| 5,998,679 A | 12/1999 | Miller | 568/859 |
| 6,150,322 A | 11/2000 | Singleton et al. | 510/426 |
| 6,403,840 B1 | 6/2002 | Zhou et al. | 568/579 |
| 6,452,058 B1 | 9/2002 | Schweizer et al. | 570/223 |
| 6,462,243 B1 | 10/2002 | Zhou et al. | 568/893 |
| 6,465,696 B1 * | 10/2002 | Zhou et al. | 568/671 |
| 6,465,699 B1 | 10/2002 | Grosso | 568/893 |
| 6,472,572 B1 | 10/2002 | Zhou et al. | 568/893 |
| 6,486,368 B1 | 11/2002 | Zhou et al. | 568/893 |
| 6,525,230 B2 | 2/2003 | Grosso | 568/891 |
| 6,706,931 B2 | 3/2004 | Edwards | 568/671 |
| 2002/0151738 A1 | 10/2002 | Edwards et al. | 558/31 |
| 2002/0183567 A1 | 12/2002 | Fenouil et al. | 568/910.5 |
| 2002/0198416 A1 | 12/2002 | Zhou et al. | 568/910 |
| 2003/0069452 A1 | 4/2003 | Sherman et al. | 568/694 |
| 2003/0120121 A1 | 6/2003 | Sherman et al. | 568/800 |
| 2003/0125589 A1 | 7/2003 | Grosso | 568/910 |
| 2003/0166973 A1 | 9/2003 | Zhou et al. | 568/488 |
| 2004/0006246 A1 | 1/2004 | Sherman et al. | 568/470 |

OTHER PUBLICATIONS

"$C_1$ Coupling *via* bromine activation and tandem catalytic condensation and neutralization over CaO/zeolite composites," by Ivan Lorkovic, Maria Noy, Mike Weiss, Jeff Sherman, Eric McFarland, Galen D. Stucky and Peter C. Ford, *The Royal Society of Chemistry 2004*, pp. 566-567.

"Catalytic Dihydroxylation of Olefins with Hydrogen Peroxide: An Organic-Solvent- and Metal-Free System," by Yoko Usui, Kazuhiko Sato, and Masato Tanaka, *Angew. Chem. Int. Ed. 2003*, 42, pp. 5623-5625.

Written Opinion for PCT/US2005/013352 of Oct. 14, 2005.

* cited by examiner

FIG. 1

PROCESS TO CONVERT LINEAR ALKANES INTO ALPHA OLEFINS

REFERENCE TO PRIOR APPLICATIONS

This application claims the benefit of U.S. Provisional application Ser. No. 60/563,966, filed Apr. 21, 2004.

FIELD OF THE INVENTION

This invention relates to the conversion of linear or branched paraffins (alkanes) into alpha olefins. More particularly, the invention relates to a process for manufacturing alpha olefins from starting materials that are linear or branched alkanes wherein chlorine or another halogen or compounds containing chlorine or another halogen are used as an intermediate in the conversion of paraffins to alpha olefins.

BACKGROUND OF THE INVENTION

Alpha olefins are used as co-monomers in polyethylene production, especially linear low density polyethylene (LL-DPE), which is a market segment that continues to grow. Other uses for alpha olefins include drilling fluids, machine lubricants, and as precursors to alcohols, esters, acids, aldehydes, $C_6$-$C_{30}$ alkylbenzenes, amines, thiols, and amine oxides. In general alpha olefins are more valuable than internal olefins, particularly for polymer applications. This invention may be used to produce alpha olefins from relatively inexpensive $C_6$-$C_{16}$ linear or branched alkanes, for example from gas-to-liquids (GTL) plants. Some of these alpha olefins ($C_6$-$C_{10}$) may be used in co-monomer applications. Previous art teaches the conversion of a higher ($C_{4+}$) paraffin to an alkyl-halide via halogenation and subsequent hydro-dehalogenation to predominantly an internal olefin such as described in U.S. Pat. Nos. 3,401,206 and 3,341,615. In addition, previous art suggests that the conversion of higher ($C_{4+}$) paraffins to alkyl-halides followed by reaction with a metal oxide or metal oxides may produce predominantly internal olefins. Examples of such prior art include U.S. Pat. Nos. 6,462,243, 6,465,699, 6,472,572, 6,486,368, and 6,465,696, all of which are herein incorporated by reference.

SUMMARY OF THE INVENTION

This invention provides a process to convert branched or linear alkanes (paraffins) to branched or linear alpha olefins of the same carbon number. Carbon numbers of particular interest are $C_4$-$C_{16}$, preferably $C_6$ to $C_{14}$, and most preferably $C_6$ to $C_{10}$.

This invention provides a process for the conversion of linear alkanes, branched alkanes, or a mixture of linear and branched alkanes into alpha olefins. The process comprises the steps of:

a) halogenating linear alkanes, branched alkanes, or a mixture of linear and branched alkanes to produce a mixture of primary mono-haloalkanes (i.e., alkanes with one halogen attached in the primary position), internal mono-haloalkanes (i.e., alkanes with one halogen attached somewhere other than the primary position), unreacted alkanes, hydrogen halide, and possibly multi-haloalkanes (i.e., alkanes with 2 or more halogens attached) wherein preferably the halogenation may be carried out thermally and/or catalytically such as in the presence of a catalyst;

b) separating the hydrogen halide produced in step a) from the other components of the mixture from step a) and optionally neutralizing it with a metal oxide or mixture of metal oxides to produce a partially halogenated metal oxide and/or metal halide or mixture of partially halogenated metal oxides and/or metal halides which may be regenerated to halogen and metal oxide (or mixture of metal oxides), preferably for recycle, using air, oxygen or gas mixtures containing oxygen gas (these mixtures may include blends of oxygen with nitrogen, argon or helium);

c) separating the primary mono-haloalkanes from the mixture of step b), preferably by distillation or other appropriate separation steps, wherein the unreacted alkanes, the multi-haloalkanes, and the internal mono-alkanes may optionally be recycled to step a);

d) reacting the separated primary mono-haloalkane, preferably by metathesis, with a metal oxide or combination of metal oxides to convert the aforesaid primary mono-haloalkane to a mixture of products that contains alpha olefins, unconverted primary mono-haloalkanes, and possibly other reaction products (such as internal olefins, primary alcohols and internal alcohols), and a partially halogenated metal oxide and/or metal halide or a mixture of partially halogenated metal oxides and/or metal halides which may be regenerated;

e) regenerating the partially halogenated metal oxide and/or metal halide or a mixture of partially halogenated metal oxides and/or metal halides to halogen (such as $Br_2$) and/or acid (such as HCl) and a metal oxide or mixture of metal oxides by reaction with air, oxygen or gas mixtures containing oxygen gas (these mixtures may include blends of oxygen with nitrogen, argon, or helium) wherein the halogen produced may optionally be recycled to step a); and f) removing the unreacted primary mono-haloalkane, which may be optionally recycled to step d), from the reaction mixture and then purifying the alpha olefins.

DETAILED DESCRIPTION OF THE INVENTION

The present invention provides a process to convert alkanes directly to valuable alpha olefins. Alkanes with carbon numbers of particular interest are $C_6$ to $C_{18}$. Linear alkanes, branched alkanes, or a combination of linear and branched alkanes may be converted via halogenation to a mixture of primary mono-haloalkanes, internal mono-haloalkanes, unreacted alkanes, hydrogen halide, and possibly multi-haloalkanes. Halogenation may preferably be carried out thermally or catalytically (for example in a conventional reactor, in a catalytic distillation (CD) column, etc.), and with or without the use of a catalyst support intended to promote shape selectivity. Halogenation processes that preferentially produce primary mono-haloalkanes (e.g., catalytic halogenation at lower temperatures, thermal halogenation at higher temperatures, etc.) are preferred. Preferred halogens are chlorine, bromine, and iodine. Particularly preferred is chlorine.

Thermal halogenation is carried out by introducing the halogen and the alkane to a reactor and heating the reactants within a temperature range for thermal halogenation of from about 100° C. to about 400° C. As stated above, catalytic halogenation may be carried out at lower temperature, such as from about 25° C. to about 400° C. Catalysts which may be used include compounds and/or complexes containing Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B Al, Ga, In, Tl, Si, Ge, Sn, Pb, P, Sb, Bi, S, Cl, Br, F, Sc, Y, Mg, Ca, Sr, Ba, Na, Li, K, O, La, Ce, Pr, Nd, Sm, Eu, Gd, Tb, Er, Yb, Lu and Cs or mixtures thereof. The amount of catalyst used will vary with the specific catalyst used and the reaction conditions selected but will range from about 0.00001 grams to about 100 grams of catalyst per gram of alkane passed over the catalyst per hour. The reaction may also be conducted in the presence of a diluent such as nitrogen, helium or argon. The process may be conducted at pressures ranging from about 0.1 atm to about 100 atm pressure.

To improve the selectivity to primary mono-halogenated products, the halogenation step may be conducted in the presence of a shape selective catalyst that favors halogenation at the ends of the alkane more than at internal positions of the paraffin. Such a catalyst would enhance the conversion of alkane to primary mono-halide. The selective bromination of halo-aromatic compounds is known to occur with some zeolite catalysts, such as described by Th. M. Wortel et al. in the Journal of Catalysis 60,110-120 (1979), which is herein incorporated by reference. The ability to improve the selectivity to primary mono-halogenated alkanes is desirable. By selecting a molecular sieve with a pore diameter close to that of the critical diffusion diameter of the alkane to be halogenated in this process, the selectivity to primary mono-halogenated alkane may be increased.

The mixture of primary mono-haloalkanes, other mono- and multi-haloalkanes, unreacted alkanes, and hydrogen halide is preferably transferred to a separation train that isolates the primary mono-haloalkanes from the mixture. The separation train may include (1) a distillation or other appropriate separation step to recover hydrogen halide, (2) a distillation or other appropriate separation step (or multiple steps) to separate unreacted alkanes, multi-haloalkanes, and mono-haloalkanes, and (3) an additional separation step to separate primary mono-haloalkanes from internal mono-haloalkanes. It may be desirable to isomerize the internal mono-haloalkanes to primary mono-haloalkanes or to convert the mono- and multi-haloalkanes to olefins via dehydrohalogenation or back to alkanes via dehalogenation/hydrogenation. The alkanes converted in this manner may be recycled back to the primary halogenation reactor and/or a disproportionation reactor.

The unreacted alkanes may also be recycled to the primary halogenation reactor and/or a disproportionation reactor. The multi-haloalkanes may be recycled to the primary halogenation reactor or may be recycled to a separate disproportionation reactor. The disproportionation reactor converts some of the multi-haloalkanes in the presence of alkanes to mono-haloalkanes. When the multi-haloalkanes are recycled to the halogenation reactor and fresh alkanes are also sent to the reactor, the halogenation reactor also serves as a disproportionation reactor. If a separate disproportionation reactor is used, the resulting reaction mixture of multi-haloalkanes and mono-haloalkanes is then recycled to the separation train. The internal mono-haloalkanes may be recycled to the primary halogenation reactor or may be recycled to an isomerization reactor to convert some of the internal mono-haloalkanes to primary mono-haloalkanes. If an isomerization reactor is used, the resulting reaction mixture of internal mono-haloalkanes and primary mono-haloalkanes is then recycled to the separation train.

Suitable separation schemes include distillation, extractive distillation, adsorption, melt crystallization, and others. For the primary and internal mono-haloalkanes, separation, distillation, and melt crystallization are particularly preferred. The ability to separate the primary mono-haloalkanes from the internal mono-haloalkanes may also be facilitated by the formation of adducts. For some carbon chain lengths ($C_6$-$C_{10}$), distillation is preferred because of differences in boiling points (and as a result, relative volatilities). For other carbon chain lengths ($C_{11}$-$C_{16}$), melt crystallization is preferred because of the substantial freezing point difference between primary and internal mono-haloalkanes.

Distillation may be used to separate many of the products of the halogenation reaction because paraffins, mono-haloalkanes, and multi-haloalkanes of the same carbon number boil at temperatures that are quite different. For example, at 760 torr n-hexane boils at 69° C., mono-chlorohexanes boil at between 122-135° C., and di-chlorohexanes boil around 160-205° C. The bromoalkanes boil at even higher temperatures, mono-bromohexanes boil at between 141-155° C., and di-bromochlorohexanes boil around 180-245° C. Hexenes boil at temperatures below that of mono-halohexanes and di-halohexanes. Similar trends are seen with other carbon numbers. For example, at 760 torr n-octane boils at 126° C., mono-chlorooctanes boil around 165-185° C., and di-bromooctanes boil above 225° C. Branched halogenated alkanes may also be separated from non-halogenated branched alkanes by distillation. For example, 3-chloro-methylheptane boils at 174° C. while 3-methylheptane boils at 115-118° C. at a pressure of 760 torr. If mixtures of alkanes are used to make mixtures of alpha olefins, separation by distillation may be more difficult.

The hydrogen-halide produced in the halogenation reactor is separated and neutralized with a metal oxide or mixture of metal oxides to produce a partially or fully halogenated metal oxide and/or metal halide or mixture of partially or fully halogenated metal oxides and/or metal halides which are then converted to halogen and metal oxide (or mixture of metal oxides) for recycle using air, oxygen or gas mixtures containing oxygen gas. These mixtures may include blends of oxygen with nitrogen, argon or helium.

Engineering configurations to carry out this hydrogen halide neutralization process include a single reactor, parallel reactors, two reactors (one to trap hydrogen halide and one to regenerate metal-halide), among others. Multiple reactors in series may also be utilized. A number of materials are known to trap or neutralize acidic hydrogen halides. These include bases such as alkali and alkaline earth hydroxides or mixtures thereof. For example, KataLeuna Lime, a mixture of calcium hydroxide and sodium hydroxide may purify hydrocarbon streams containing HCl.

Metal oxides or partially halogenated metal oxides which may be used in this step and in the metathesis reaction below, include oxides or oxyhalides of the following metals: Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, La, Ce, Pr, Nd, Sm, Eu, Gd, Tb, Er, Yb, Lu, and Cs or mixtures thereof. The amount of catalyst used will vary with the specific catalyst used and the reaction conditions selected but may range from about 0.00001 grams to about 100 grams of catalyst per gram of material passed over the catalyst per hour. The reaction may also be conducted in the presence of a diluent such as nitrogen, helium and argon. The process may be conducted at pressures ranging from about 0.1 atm to about 100 atm pressure.

The primary mono-haloalkane that is isolated in the separation train is reacted (oxidized) in a reactor, preferably a metathesis reactor, with a selected metal oxide or a combination of metal oxides to convert the primary mono-haloalkane to a mixture of products that contains alpha olefins, the unconverted primary mono-haloalkanes, and possible other reaction products. The metal oxide or combination of metal oxides is selected in order to maximize the amount of alpha olefin produced. Reaction conditions such as residence time, temperature, and reaction phase (such as solid-gas or solid-liquid) are selected to maximize alpha olefin production. The same metal oxide or combination of metal oxides may be able to produce preferentially different products (such as alcohols instead of olefins) depending on the reaction conditions. For example, shorter residence time, lower temperatures, and solid-gas phase reaction tend to preferentially produce olefins over alcohols.

The metal oxide or metal oxides used in the metathesis reactor may or may not be different from the one(s) used in the neutralization of the hydrogen halide. The metal oxide is normally partially converted (but it could be totally converted if desired) to a metal halide and or partially halogenated metal oxide. The unreacted primary mono-haloalkane is removed from the alpha olefin and possible other reaction products. Recovered alpha olefin is further purified, as needed, to obtain the desired final product. A purification train may be used to isolate the alpha olefin product. Suitable purification schemes include distillation, adsorption, melt crystallization, and others. The unconverted primary mono-haloalkane may preferably be recycled to the metathesis reactor.

The metal halide and/or partially halogenated metal oxide may be regenerated to a metal oxide or a mixture of metal oxides and halogen (e.g. $Cl_2$) by using air, oxygen, or gas mixtures containing oxygen gas. These mixtures may include blends of oxygen with nitrogen (such as 1 wt. % oxygen in nitrogen), argon or helium. The liberated halogen (e.g. $Cl_2$) is recycled to the halogenation reactor. If water is also present in the system, hydrogen halide may also be produced. The regeneration of the metal halide and/or partially halogenated metal oxide to metal oxide and halogen may be accomplished with various reactor configurations including a separate regeneration reactor, in situ with a combined regeneration/metathesis reactor wherein the regeneration gas (such as air, oxygen, etc) flow and primary alkane feed flow are alternated, in situ regeneration with a multiple metathesis reactor configuration in a fixed bed mode, etc. The same steps may be used when a combination of metal oxides and/or partially halogenated metal oxides are used.

Recovered alpha olefin is further purified, as needed, to obtain the final product.

Figure 1:
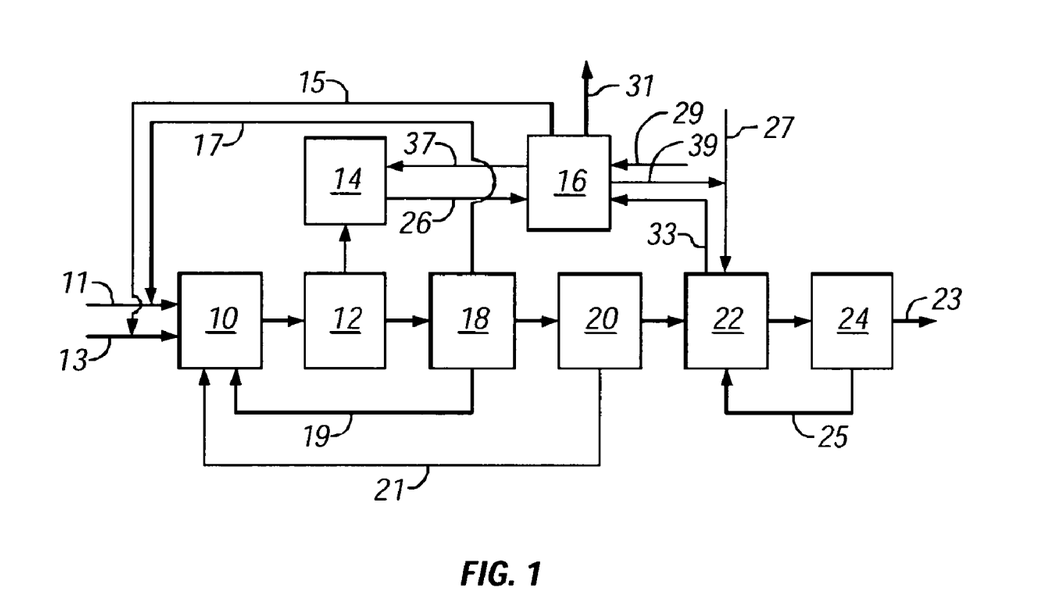
FIG. 1 is a block flow diagram for the production of alpha olefins from their corresponding alkanes.

One embodiment of the process is illustrated in FIG. 1. Linear alkanes, branched alkanes, or a mixture of linear and branched alkanes from feed line 11 are converted via halogenation in reactor 10 by reaction with halogen from feed line 13 to a mixture of primary mono-haloalkanes, other mono-haloalkanes, unreacted alkanes, hydrogen halide, and possibly multi-haloalkanes. The mixture of primary mono-haloalkanes, internal mono- and multi-haloalkanes, unreacted alkanes, and hydrogen halide is transferred to a separation vessel 12 to remove the hydrogen halide.

The hydrogen halide is transferred to a neutralization reactor 14 where it is contacted with a metal oxide or combination of metal oxides to form a metal halide(s) and/or a partially halogenated metal oxide(s). The metal halide(s) and/or a partially halogenated metal oxide(s) is transferred through line 26 to regeneration reactor 16 and regenerated therein with air, oxygen, or gas mixtures containing oxygen gas from feed line 29 to recover the metal oxide(s), which may be recycled to the neutralization reactor 14 through line 37, and the halogen, which may be recycled through recycle line 15 to the halogenation reactor 10. The gas mixtures used may include blends of oxygen with nitrogen, argon, or helium. Excess oxygen and/or spent air are removed through line 31.

The remaining mixture of primary mono-haloalkanes, internal mono- and multi-haloalkanes, and unreacted alkanes from separation vessel 12 is transferred to separation vessel 18, where the unreacted alkane and the multi-haloalkanes are separated and then may be recycled to halogenation reactor 10 through alkane recycle line 17 and multi-haloalkanes recycle line 19. The remaining mixture of mono-haloalkanes (primary and internal) is transferred to a separation vessel 20 to isolate the primary mono-haloalkanes. The internal mono-haloalkanes may be recycled to the halogenation reactor 10 through recycle line 21.

The primary mono-haloalkane is reacted in metathesis reactor 22 with a selected metal oxide or a combination of metal oxides (an example of the combination of metal oxides is CuO on $ZrO_2$) to convert the primary mono-haloalkane to a mixture of products that contains alpha olefins and unconverted primary mono-haloalkanes. The metal oxide enters metathesis reactor 22 through line 27 which may contain metal oxide from the regenerator 16 which is combined with line 27 through line 39. The metal oxide(s) is partially converted to a metal halide(s) and/or partially halogenated metal oxide(s) which may be recycled to the regeneration reactor 16 through line 33.

A purification train 24 (which may include one or more separation vessels or steps) is used to separate alpha olefins from unconverted primary mono-haloalkanes and other reaction products. The alpha olefins are recovered through product stream 23. The unconverted primary mono-haloalkane may be recycled to the metathesis reactor 22 through recycle line 25. Recovered alpha olefin is further purified, as needed, to obtain the final product.

Although one embodiment of the invention has been shown in FIG. 1 and described above, it is understood that the invention is not limited to such embodiment or to the embodiments disclosed, but is capable of numerous rearrangements, modifications, and substitutions of parts and elements without departing from the spirit of the invention.

In another embodiment, a separate disproportionation reactor may be utilized. In another embodiment, an isomerization reactor that converts the internal mono-haloalkanes into primary mono-haloalkanes may be employed. In another embodiment, an isomerization reactor and a disproportionation reactor may both be used. In all of the embodiments of this invention, a halogenation step is required. Disproportionation, isomerization, dehydrohalogenation, and dehalogenation combined with hydrogenation are all process steps which may or may not be included in the process, depending upon the desired products and economics.

Examples 1-3 below illustrate the thermal isomerization of internal monohaloalkanes into primary monohaloalkanes.

EXAMPLE 1

Thermal Isomerization of Mono-chlorohexane

To demonstrate the conversion of an internal mono-chloroalkane into a primary mono-chloroalkane, 3.5 grams of 2-chlorohexane (purchased from TCI America) was added to a small Parr acid digestion bomb. The top of digestion bomb was screwed on and tightened to prevent leaking. The digestion bomb was placed in an oven and the contents allowed to react at 250° C. for 16 hours. The 2-chlorohexane used had a purity of 98.8% by GC and contained less than 0.1% 1-chlorohexane. The contents were analyzed and found to contain 3.6% 1-chlorohexane. No catalyst was used—the material isomerized on its own. The remaining material was made up of similar amount of 2-chlorohexane and 3-chlorohexane.

EXAMPLE 2

Thermal Isomerization of Mono-chlorohexane

In another experiment, 3.5 grams of 2-chlorohexane (purchased from TCI America) was added to a small Parr acid digestion bomb. The digestion bomb was sealed and placed in an oven heated to 200° C. The contents were allowed to react for a period of 16 hours and then analyzed and found to contain 1.8% 1-chlorohexane. No catalyst was used—the material isomerized on its own. The remaining material was made up of primarily 2-chlorohexane and some 3-chlorohexane.

EXAMPLE 3

Thermal Isomerization of Mono-bromohexane

To demonstrate the conversion of an internal mono-bromoalkane into a primary mono-bromoalkane, 3.5 grams of 2-bromohexane (purchased from Lancaster Synthesis Inc.) was added to a small Parr acid digestion bomb. The 2-bromohexane used had a purity of 99.2% by GC and contained less than 0.1% 1-Bromohexane. The digestion bomb was placed in oven and allowed to react at 250° C. for 16 hours, the contents were analyzed and found to contain 3.5% 1-bromohexane. No catalyst was used—the material isomerized on its own. The remaining material was made up of 2-bromohexane and 3-bromohexane.

Examples 4-8 describe the preparation of catalysts which are then used in Examples 9-16 for catalytic isomerization of internal monohaloalkanes into primary monohaloalkanes.

EXAMPLE 4

Preparation of 0.1 Wt. % Pd on Magnesium Silicate Catalyst

Magnesium silicate extrudates (0.8 mm trilobes) were obtained from CRI Inc. The desired amount of palladium was incorporated into the magnesium silicate by pore volume impregnation of the dried extrudates with an aqueous tetraammine palladium chloride solution containing the desired amount of Pd. The impregnated extrudates were dried at 125° C. for eight hours and then calcined in flowing air at 300° C. for two hours. The cooled sample was analyzed and found to contain 0.1 Wt. % palladium.

EXAMPLE 5

Preparation of 0.1 Wt. % Pt on Magnesium Silicate Catalyst

Magnesium silicate extrudates (0.8 mm trilobes) were obtained from CRI Inc. Platinum was incorporated into the magnesium silicate by pore volume impregnation with an aqueous tetraammine platinum hydroxide solution. The extrudates were dried at 125° C. for eight hours and then calcined in flowing air at 300° C. for two hours. The cooled sample was analyzed and found to contain 0.1 Wt. % platinum.

EXAMPLE 6

Preparation of 0.07 Wt. % Pd and 0.03 Wt. % Pt on Magnesium Silicate Catalyst Magnesium silicate extrudates (0.8 mm trilobes) were obtained from CRI Inc. Platinum and palladium were incorporated into the magnesium silicate by pore volume impregnation with a mixture of aqueous tetraammine palladium chloride solution and tetraammine platinum hydroxide solution. The extrudates were dried at 125° C. for eight hours and then calcined in flowing air at 300° C. for two hours. The cooled sample was analyzed and found to contain 0.07 Wt. % palladium and 0.03 Wt. % platinum.

EXAMPLE 7

Preparation of 0.1 Wt. % Pd and 0.1 Wt. % Bi on Magnesium Silicate Catalyst

Magnesium silicate extrudates (0.8 mm trilobes) were obtained from CRI Inc. Palladium and bismuth were incorporated into the magnesium silicate by pore volume impregnation with aqueous tetraammine palladium nitrate and aqueous bismuth nitrate. The impregnated extrudates were dried at 125° C. for eight hours and then calcined in flowing air at 300° C. for two hours. The cooled sample was analyzed and found to contain 0.1 Wt. % palladium and 0.1 Wt. % bismuth.

EXAMPLE 8

Preparation of 0.20 Wt. % Pd and 0.20 Wt. % Sn on Magnesium Silicate Catalyst Magnesium silicate extrudates (0.8 mm trilobes) were obtained from CRI Inc. Platinum and tin were incorporated into the magnesium silicate by pore volume impregnation with aqueous tetraammine palladium chloride and aqueous tin chloride ($SnCl_4$). The impregnated extrudates were dried at 125° C. for eight hours and then calcined in flowing air at 300° C. for two hours. The cooled sample was analyzed and found to contain 0.2 Wt. % palladium and 0.2 Wt. % tin.

EXAMPLES 9 to 13

Catalytic Isomerization of 2-bromohexane

To demonstrate the catalytic conversion of an internal mono-bromoalkane into a primary mono-bromoalkane, 3.5 grams of 2-bromohexane (purchased from Lancaster Synthesis Inc.) was added to five Parr acid digestion bombs. The 2-bromohexane used had a purity of 99.2% by GC and contained less than 0.1% 1-bromohexane. To the five Parr digestion bombs was added 0.10 grams of the magnesium silicate catalysts described in Examples 4 to 8. The digestion bombs were sealed, placed in an oven, and allowed to react at 250° C. for 16 hours. The contents of each digestion bomb were analyzed separately and found to contain between 4.9 and 7.6% 1-bromohexane as shown in Table 1. The remaining material was made up of mainly 2-bromohexane and 3-bromohexane although some olefins were also produced.

TABLE 1

| Example | Catalyst Used Prepared in | 1-Bromohexane in Product, (% Wt.) |
|---|---|---|
| 9 | Example 4 (Pd) | 5.3 |
| 10 | Example 5 (Pt) | 4.6 |
| 11 | Example 6 (Pd/Pt) | 5.0 |
| 12 | Example 7 (Pd/Bi) | 7.3 |
| 13 | Example 8 (Pd/Sn) | 7.6 |

EXAMPLES 14 to 16

Catalytic Isomerization of 2-Chlorohexane

To demonstrate the catalytic conversion of an internal mono-chloroalkane into a primary mono-chloroalkane, 3.5 grams of 2-chlorohexane (purchased from TCI America) was added to three Parr acid digestion bombs. The 2-chlorohexane used had a purity of 98.8% by GC and contained less than 0.1% 1-chlorohexane. To the three Parr digestion bombs was added 0.10 grams of the magnesium silicate catalysts described in Examples 5, 7, and 8. The digestion bombs were sealed, placed in an oven, and allowed to react at 250° C. for 16 hour. The contents of each digestion bomb were analyzed separately and found to contain between 4.6 and 7.5% 1-chlorohexane as shown in Table 2. The remaining material was made up of mainly 2-chlorohexane and 3-chlorohexane although some olefins were also produced.

TABLE 2

| Example | Catalyst Used Prepared in | 1-Chlorohexane in Product, (% Wt.) |
|---|---|---|
| 14 | Example 5 (Pt) | 4.6 |
| 15 | Example 6 (Pd/Pt) | 5.1 |
| 16 | Example 8 (Pd/Sn) | 7.5 |

As may be seen in Tables 1 and 2, the concentration of the 1-haloalkane isomer may be increased by isomerizing an internal haloalkane, such as 2-bromohexane, into the 1-haloalkane isomer.

The Conversion of Haloalkanes into Alkanes for Recycling to a Halogenation Reactor The ability to convert chlorinated propane into propylene by reaction with hydrogen in the presence of a catalyst has been described in U.S. Pat. No. 5,821,394, which is herein incorporated by reference. U.S. Pat. No. 3,892,818, also herein incorporated by reference, describes a process for converting 1,2-di-chloropropane into essentially propane ($C_3H_8$) using hydrogen and an expensive catalyst containing both rhodium and gold. The conversion of heavier (higher carbon number) mono-haloalkanes and multi-haloalkanes into alkanes for recycle to the halogenation reactor is one of the embodiments of this invention. By converting the (higher carbon number) multi-haloalkanes and/or internal mono-haloalkanes into alkanes that may be sent back to a halogenation reactor, additional amounts of primary mono-haloalkanes (such as 1-chlorodecane) may be produced. The following examples 17-21 illustrate how haloalkanes may be converted into olefins and/or alkanes by passing the haloalkanes over a catalyst or a combination of catalysts if desired.

The Conversion of a Mixture of Chlorohexanes into Hexanes.

An 1:1:1 mixture of 1-chlorohexane, 2-chlorohexane, and 3-chlorohexane is prepared by blending together equal weights of each of the chlorohexanes. The chlorohexanes are converted to hexane by passing the chlorohexanes over a catalyst(s) in the presence of hydrogen, at a reaction temperature of about 100 to about 400° C., preferably about 200 to about 350° C., in the liquid or gas phase. Although the reaction may be carried at an operating pressure ranging from about 10 bar to about 100 bar, it is preferable to operate the process at a pressure of about 15 bar to about 50 bar, most preferably about 15 bar to about 30 bar. The use of lower pressure and temperature may limit the rate of hydrogenation while too high a pressure and temperature used may result in the production of unwanted hydrocracking of the reactants to less desirable lighter molecules. It is possible to produce a larger amount of olefins (instead of alkanes) if a reactor operating pressure of about 1 to about 10 bar is used with hydrogen.

EXAMPLE 17

Preparation of 2.0 Wt. % Pt on Magnesium Silicate Catalyst

Magnesium silicate extrudates (0.8 mm trilobes) were obtained from CRI Inc. Platinum was incorporated into the magnesium silicate by pore volume impregnation with an aqueous tetraanmine platinum hydroxide solution. The Pt containing extrudates were dried at 125° C. for eight hours and then calcined in flowing air at 300° C. for two hours. The cooled sample was analyzed and found to contain 2.0 Wt. % platinum.

EXAMPLE 18

Conversion of 1,2-di-bromohexane into Hexane

The conversion of a haloalkane into alkane was demonstrated in a laboratory dehalogenation/hydrogenation reactor. The reactor tube used was 27" long and had an 1.00" OD and 0.58" ID. A mixture of 4.00 grams of the catalyst (prepared in Example 17) and 45 grams of 80-mesh silicon carbide was centered in the reactor tube between beds of 20 mesh SiC. Once the reactor tube was loaded, the ends were attached and the reactor was placed inside a 24" long, 4-zone furnace. The furnace was used to heat the catalyst to the desired reaction temperature. The reactor was connected to the reactant supply lines and the reactor outlet line. The reactor was purged with nitrogen and then the catalyst was reduced with hydrogen at 300° C. The reactor pressure was adjusted to 20 bar and the hydrogen flow rate was maintained at 20 L/Hr. The 1,2-di-bromohexane feedstock (obtained from Aldrich Chemical Co.) was passed through the reactor at a feed rate of 24 grams per hour. The product stream was cooled to 25° C. and the pressure was dropped to atmospheric pressure. The liquid products were analyzed by NMR and GC and found to contain greater than 99% hexane.

EXAMPLE 19

Conversion of 1-bromooctane into Octane

The conversion of a halooctane into octane was demonstrated in using the reactor and test conditions described in Example 18. 1-bromooctane was passed through the reactor at a feed rate of 20 grams per hour. The product stream was cooled to 25° C. and the pressure was dropped to atmospheric pressure. The liquid products were analyzed by NMR and GC and found to contain greater than 99% octane.

EXAMPLE 20

Conversion of 1-bromooctane into Octane and Lighter hydrocarbons

The conversion of a halooctane into octane and lighter hydrocarbons was demonstrated using the reactor and test conditions described in Example 18 with the exception that a 0.35 Wt. % Pt on hydrogen mordenite catalyst was used. The catalyst was prepared by the procedure described in example 1 of U.S. Pat. No. 5,057,472. The catalyst was dried and the platinum was reduced before feed was passed over the catalyst. 1-bromohexane was passed through the reactor at a feed rate of 20 grams per hour. The product stream was cooled to 25° C. and the pressure was dropped to atmospheric pressure. The liquid products were analyzed by NMR and GC and found to contain greater than 99% alkanes. The liquid product contained more than 50% lighter alkanes ($C_1$-$C_7$) than octane which indicated that considerable cracking occurred over the highly acid zeolite catalyst. The acidic catalyst when operated under these conditions produced alkanes with a high degree of branching in the $C_4$-$C_8$ alkane fraction of the product.

Based on the results obtained in Examples 19 and 20, it is preferred to use a catalyst with less acidity in order to obtain a product with the same carbon number as the feedstock used. Preferably then, other less acidic catalyst supports such as carbon, alumina, or magnesium oxide may be used with metals such as Pt and/or Pd. Combinations of these metals with Ag, Cu, Au, Sn, Bi, Pb, Rh, Ge, Ga, Sb, and In may also be used.

EXAMPLE 21

Conversion of 1-bromooctane into Octene and Octane

The conversion of a chlorooctane into octene and octane was demonstrated using the reactor described in Example 18. In this example, the catalyst of Example 8 was reduced in flowing hydrogen. 1-chlorooctane was passed through the reactor at a feed rate of 20 grams per hour. When operating at a lower operating pressure of 5 bar, a feed rate of 24 g/hr and a hydrogen flow rate of 10 L/Hr, the liquid product was found to contain over 50% octenes with the balance octanes. Of the octenes produced, 1-octene was the most abundant octene.

Operation at a lower hydrogen pressure and the use of a catalyst with lower hydrogenation activity resulted in more olefins in the product.

Examples 22-24 show how monohaloalkanes may be produced from dihaloalkanes.

EXAMPLE 22

The Production of Mono-Bromohexanes from the Reaction of n-Hexane and 1,6 Di-Bromohexane To demonstrate the conversion of a di-haloalkane into a mono-haloalkane, 0.0174 moles of hexane and 1,6-di-bromohexane (both obtained from Aldrich Chemical Company) were added to a small Parr acid digestion bomb and sealed. The n-hexane used had a purity of 99+ % and had a total hexanes purity of >99.9%. The 1,6 di-bromohexane used had a purity of 96+ % and had a total di-bromohexanes purity of >99.6%. The bomb was heated to 225° C. and allowed to react for 4 hours. After cooling the bomb to room temperature, the vessel was opened and the contents were analyzed by gas chromatography. The product mixture was found to contain 6% mono-bromohexanes, 0.3% hexenes and less than 0.1% benzene. The balance of the material was essentially di-bromohexanes and hexanes. The concentrations of both the di-bromohexanes and hexanes in the product were lower than in the starting mixture.

EXAMPLE 23

The Production of Mono-Bromohexanes from the Reaction of n-Hexane and 1,2 Di-Bromohexane To demonstrate the conversion of another type of di-haloalkane into a mono-haloalkane, 0.0174 moles of hexane and 1,2-di-bromohexane (both obtained from Aldrich Chemical Company) were added to a small Parr acid digestion bomb and sealed. The n-hexane used had a purity of 99+ % and had a total hexanes purity of >99.9%. The 1,2 di-bromohexane used had a purity of 98+ % and had a total di-bromohexanes purity of >99.8%. The bomb was heated to 225° C. and allowed to react for 4 hours. After cooling the bomb to room temperature, the vessel was opened and the contents were analyzed by gas chromatography. The product mixture was found to contain 15.2% mono-bromohexanes, 1.5 hexenes and less than 0.3% benzene. The balance of the material was essentially di-bromohexanes and hexanes. The concentrations of both the di-bromohexanes and hexanes in the product were lower than in the starting mixture.

EXAMPLE 24

The Production of Mono-Chlorohexanes from the Reaction of n-Hexane and 1,6 Di-Chlorohexane To demonstrate the conversion of a di-haloalkane into a mono-haloalkane, 0.0174 moles of hexane and 1,6-di-chlorohexane (both obtained from Aldrich Chemical Company) were added to a small Parr acid digestion bomb and sealed. The n-hexane used had a purity of 99+ % and had a total hexanes purity of >99.9%. The 1,6 di-chlorohexane used had a purity of 98+ % and had a total di-chlorohexanes purity of >99.7%. The bomb was heated to 225° C. and allowed to react for 4 hours. After cooling the bomb to room temperature, the vessel was opened and the contents were analyzed by gas chromatography. The product mixture was found to contain 3% mono-chlorohexanes, 3% hexenes and less than 0.1% benzene. The balance of the material was essentially di-chlorohexanes and hexanes. The concentrations of both the di-chlorohexanes and hexanes in the product were lower than in the starting mixture. Of the hexenes present in the product, 85% of the hexenes were in the form of 1-hexene.

Example 25 illustrates the halogenation of alkanes to produce haloalkanes.

EXAMPLE 25a

Primary Bromination of Octane

A 4 inch glass tube reactor was loaded with glass beads and heated to 250° C. A syringe pump was used to deliver 40 microliter per minute of normal octane into the top of the reactor. Also to the top of the flow reactor was delivered 5 milliliters per minute of bromine in the gas phase. The product material was collected at the bottom of the flow reactor and tested to contain about 1% primary bromo octane, and about 99% internal bromo octanes.

EXAMPLE 25b

Primary Bromination of Octane Using Chlorine to Enhance Results

A 4 inch glass tube reactor was loaded with glass beads and heated to 250° C. A syringe pump was used to deliver 40 microliter per minute of normal octane into the top of the reactor. Also to the top of the flow reactor was delivered 5 milliliters per minute of bromine in the gas phase. In addition, the pressure of chlorine gas in the system was kept at 5 psi. The product material was collected at the bottom of the flow reactor and tested to contain about 7% primary bromo octane and 93% internal bromo octanes. Chlorine should be used in an amount no more than the amount of bromine used. Preferably, the bromine and chlorine should be used in about a 1:1 molar ratio.

EXAMPLE 25c

Primary Chlorination of Octane

A 2 inch glass tube reactor was loaded with glass beads and heated to 200° C. A syringe pump was used to deliver 40 microliter per minute of normal octane into the top of the reactor. Also to the top of the flow reactor was delivered chlorine gas and the system was kept at 10 psi chlorine. The product material was collected at the bottom of the flow reactor and tested to contain about 17% primary chloro octane and 83% internal chloro octanes.

Example 26 illustrates the metal oxide catalyzed reaction of primary haloalkanes to primary alcohols and olefins.

EXAMPLE 26a

Primary Bromide Dodecane to a Primary Alcohol and Primary Olefin

To a 3 ml stainless steel batch reactor was charged approximately 0.25 grams of solid metal oxide, comprising 15% Fe and 85 wt % MgO. To this was added 0.25 grams of a mixture of 80 wt % octadecane and 20 wt % 1-bromo dodecane. The solid and liquid were mixed together. The reactor was sealed and heated to 200° C. for 3 hours. The reactor was cooled and the contents were analyzed by GC. 75% of the 1-bromo dodecane was converted. The products were 62% 1-dodecanol, 32% di-dodecanyl ether, and 6% dodecene.

EXAMPLE 26b

Primary Chloride Dodecane to a Primary Alcohol and Primary Olefin

To a 3 ml stainless steel batch reactor was charged approximately 0.25 grams of solid metal oxide, comprising 15% Fe and 85 wt % MgO. To this was added 0.25 grams of a mixture of 80 wt % octadecane and 20 wt % 1-chloro dodecane.

The solid and liquid were mixed together. The reactor was sealed and heated to 200° C. for 3 hours. The reactor was cooled and the contents were analyzed by GC. 45% of the 1-chloro dodecane was converted. The products were 84% 1-dodecanol, 13% di-dodecanyl ether, and 3% dodecene.

Example 27 illustrates the regeneration of the metal halogens to produce halogen.

EXAMPLE 27a

Metal Bromide Regeneration to Yield Bromine Gas

A 4 inch glass tube reactor was loaded with spent 15 wt % Fe 85 wt % MgO metal oxide catalyst which contained metal bromide. The catalyst was placed between beds of glass beads. The tube was heated to 325° C. while a mixture of nitrogen, oxygen and water was past over the spent metal catalyst. The off gas was past through an IR cell and the amount of HBr was monitored. The off gas was also titrated for $Br_2$ content. As the temperature approached 300° C., the regeneration reaction started and bromine gas was produced. After 30 minutes at 325° C., the metal oxide had finished regenerating and the bromine had been taken off the metal oxide as bromine gas without the production of HBr.

EXAMPLE 27b

Metal Chloride Regeneration to Yield Chlorine Gas

A 4 inch glass tube reactor was loaded with spent 15 wt % Fe 85 wt % MgO metal oxide catalyst which contained metal chloride. The catalyst was placed between beds of glass beads. The tube was heated to 525° C. while a mixture of nitrogen, oxygen and water was past over the spent metal catalyst. The off gas was past through an IR cell and the amount of HCl was monitored. The off gas was also titrated for $Cl_2$ content. As the temperature approached 500° C., the regeneration reaction started and a mixture of chlorine gas and HCl were produced. After 4 hours at 525° C., the metal oxide had finished regenerating and the chlorine had been taken off the metal oxide in the ratio of 25% wt HCl and 75 wt % Chlorine.

We claim:

1. A process for the conversion of alkanes to alpha olefins which comprises:
    a) halogenating linear alkanes, branched alkanes, or a mixture of linear and branched alkanes to produce a mixture of primary mono-haloalkanes, internal mono-haloalkanes, unreacted alkanes, hydrogen halide, and possibly multi-haloalkanes wherein the halogenation is carried out thermally and/or catalytically;
    b) separating the hydrogen halide produced in step a) from the other components of the mixture from step a) and optionally neutralizing it with a metal oxide or mixture of metal oxides to produce a partially halogenated metal oxide and/or metal halide or mixture of partially halogenated metal oxides and/or metal halides;
    c) separating the primary mono-haloalkanes from the mixture of step b);
    d) reacting the separated primary mono-haloalkanes with a metal oxide or combination of metal oxides to convert the primary mono-haloalkanes to a mixture of products that contains alpha olefins, unconverted primary mono-haloalkanes, and possibly other reaction products; and also contains a partially halogenated metal oxide and/or metal halide or a mixture of partially halogenated metal oxides and/or metal halides;
    e) regenerating the partially halogenated metal oxide and/or metal halide or a mixture of partially halogenated metal oxides and/or metal halides to halogen and/or acid and a metal oxide or mixture of metal oxides; and
    f) removing the unreacted primary mono-haloalkanes from the alpha olefins and then purifying the alpha olefins;
    wherein the internal mono-haloalkanes are recycled and reacted in a separate isomerization reactor to convert some of the internal mono-haloalkanes to primary mono-haloalkanes which are then recycled to step (d).

2. The process of claim 1 wherein step a) is carried out in the presence of a catalyst.

3. The process of claim 1 wherein the neutralization of step b) is carried out and the halogen is regenerated and recycled to step a) and the metal oxide is regenerated.

4. The process of claim 1 wherein at least one of the unreacted alkanes, the multi-haloalkanes, and the internal mono-haloalkanes from step c) are recycled to step a).

5. The process of claim 1 wherein the reaction of step d) is carried out by metathesis.

6. The process of claim 1 wherein the halogen produced in step e) is recycled to step a).

7. The process of claim 1 wherein the unreacted primary mono-haloalkane from step f) is recycled to step d).

8. The process of claim 1 wherein the regeneration of step e) is carried out using air, oxygen or gas mixtures containing oxygen gas which are selected from the group consisting of blends of oxygen with nitrogen, argon, or helium.

9. The process of claim 1 wherein the partially halogenated metal oxide and/or metal halide or mixture of partially halogenated metal oxides and/or metal halides is regenerated to a metal oxide or a mixture of metal oxides which is then used in step d) and/or to neutralize the hydrogen halide in step b).

10. The process of claim 1 wherein the halogenation is carried out thermally within the temperature range of from about 100° C. to about 400° C.

11. The process of claim 1 wherein the halogenation is carried out in the presence of a catalyst at a temperature from about 25° C. to about 400° C.

12. The process of claim 1 wherein the multi-haloalkanes are reacted in a separate disproportionation reactor to produce a mixture of multi-haloalkanes and mono-haloalkanes which is recycled to step b) or step c) or both.

13. The process of claim 1 wherein the halogen is selected from the group consisting of bromine and chlorine.

14. The process of claim 13 wherein the halogen is bromine.

15. The process of claim 14 wherein chlorine is used in an amount no more than the amount of bromine used to increase the amount of primary bromoalkane produced.

* * * * *